United States Patent
Takagi

(10) Patent No.: US 10,255,247 B2
(45) Date of Patent: Apr. 9, 2019

(54) PUNCTURE PLANNING APPARATUS AND PUNCTURE SYSTEM

(71) Applicant: CANON KABUSHIKI KAISHA, Tokyo (JP)

(72) Inventor: Kiyoshi Takagi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 708 days.

(21) Appl. No.: 14/791,602

(22) Filed: Jul. 6, 2015

(65) Prior Publication Data
US 2016/0008082 A1 Jan. 14, 2016

(30) Foreign Application Priority Data

Jul. 10, 2014 (JP) .................................. 2014-142425
Apr. 15, 2015 (JP) .................................. 2015-083663

(51) Int. Cl.
*A61B 17/34* (2006.01)
*G06F 17/10* (2006.01)
(Continued)

(52) U.S. Cl.
CPC .......... *G06F 17/10* (2013.01); *A61B 17/3403* (2013.01); *A61B 34/10* (2016.02);
(Continued)

(58) Field of Classification Search
None
See application file for complete search history.

(56) References Cited

U.S. PATENT DOCUMENTS 5,313,897 A * 5/1994 Katamine ............ B25J 15/0019
112/470.13
6,574,493 B2 * 6/2003 Rasche .................... A61B 6/12
600/407
(Continued)

FOREIGN PATENT DOCUMENTS

JP 2006-271546 10/2006
JP 2009-226087 10/2009
(Continued)

OTHER PUBLICATIONS

Office Action dated Oct. 2, 2018, in counterpart Japanese application 2015-083663 (7 pages).

*Primary Examiner* — Kibrom K Gebresilassie
(74) *Attorney, Agent, or Firm* — Venable LLP

(57) ABSTRACT

A puncture planning apparatus has: a simulation unit that simulates movement of an organ and a puncture needle by simulation using an organ model; and a planning unit that plans, based on the simulation result, how to move the puncture needle when an actual organ is punctured. The simulation unit executes a plurality of times of the simulation of an operation to advance the puncture needle while correcting an angle of the puncture needle so as to follow the movement of the target segment due to deformation of the organ, conditions of an advancement speed of the puncture needle are changed for each of the plurality times of the simulation, and the planning unit performs planning using the best simulation result out of the plurality of simulation results acquired under different conditions of the advancement speed.

6 Claims, 15 Drawing Sheets

(51) Int. Cl.
- *A61B 34/30* (2016.01)
- *A61B 34/10* (2016.01)
- *G16H 50/50* (2018.01)
- *G06F 19/00* (2018.01)
- *A61B 8/08* (2006.01)
- *A61B 90/11* (2016.01)
- *A61B 5/06* (2006.01)
- *A61B 34/20* (2016.01)
- *G01R 33/28* (2006.01)

(52) U.S. Cl.
CPC .............. A61B 34/30 (2016.02); G06F 19/00 (2013.01); G16H 50/50 (2018.01); *A61B 5/065* (2013.01); *A61B 8/0841* (2013.01); *A61B 17/3478* (2013.01); *A61B 34/20* (2016.02); *A61B 90/11* (2016.02); *A61B 2017/3413* (2013.01); *A61B 2034/104* (2016.02); *A61B 2034/107* (2016.02); *G01R 33/287* (2013.01)

(56) References Cited

U.S. PATENT DOCUMENTS

| | | | | |
|---|---|---|---|---|
| 7,955,321 B2* | 6/2011 | Kishi | ...................... | A61B 34/70 600/410 |
| 8,032,320 B2* | 10/2011 | Sato | ................... | A61B 1/00158 702/94 |
| 8,244,327 B2* | 8/2012 | Fichtinger | .............. | A61B 5/055 600/407 |
| 8,521,257 B2* | 8/2013 | Whitcomb | .............. | A61B 5/055 600/411 |
| 8,529,433 B2* | 9/2013 | Kawano | ............. | A61B 1/00087 600/101 |
| 8,632,468 B2* | 1/2014 | Glossop | .................. | A61B 34/20 600/424 |
| 9,662,138 B2* | 5/2017 | Takagi | ............... | A61B 17/3403 |
| 9,788,901 B2* | 10/2017 | Popovic | ................... | A61B 1/00 |
| 2007/0016067 A1* | 1/2007 | Webster, III | ....... | A61B 17/3403 600/464 |
| 2008/0234700 A1* | 9/2008 | Trovato | ................. | A61B 90/10 606/139 |
| 2008/0306340 A1* | 12/2008 | Uchiyama | .......... | A61B 1/00158 600/117 |
| 2009/0149867 A1* | 6/2009 | Glozman | ........... | A61B 17/3478 606/130 |
| 2010/0179381 A1* | 7/2010 | Kawano | ............. | A61B 1/00087 600/104 |
| 2010/0312129 A1* | 12/2010 | Schecter | .............. | A61B 5/0031 600/508 |
| 2015/0150591 A1* | 6/2015 | Takagi | ............ | A61B 17/00234 606/185 |

FOREIGN PATENT DOCUMENTS

| | | |
|---|---|---|
| JP | 2011-125420 A | 6/2011 |
| JP | 2014-4212 A | 1/2014 |

* cited by examiner

PUNCTURE PLANNING APPARATUS AND PUNCTURE SYSTEM

BACKGROUND OF THE INVENTION

Field of the Invention

The present invention relates to a technique to perform planning for puncture.

Description of the Related Art

Minimal invasive treatment is an effective treatment method, which exerts minimal physical burden on a patient and can reduce post operative medical treatment and decrease a rehabilitation period, and is advantageous in terms of reducing medical cost. A minimal invasive percutaneous treatment method that is attracting attention is a localized treatment, where a puncture needle is inserted into an organ from outside the body, and a radio wave, a microwave, a laser or the like is irradiated causing necrosis of tumor tissue.

In the puncture treatment, it is demanded that the puncture needle is accurately inserted so that the tip of the puncture needle reaches a target segment, such as a tumor. For this reason, puncture is normally performed while checking the position of the target, such as a tumor, in an intravital image acquired by ultrasound, CT, MRI or the like. However, the needle may bend or the intravital tissue may deform when the needle is inserted, hence it is not easy for the tip of the needle to accurately reach the target segment, even if guidance based on an intravital image is used.

Therefore a method of using computer simulation with an organ model has been proposed as a prior art emphasizing accurate puncture. For example, Japanese Patent Application Laid-open No. 2006-271546 discloses a method for correcting a path of the needle using a puncture robot by recognizing the actual bending and position of the needle by a force sensor and image information, and predicting the operation of the needle in the organ by simulation using a model of the organ.

Japanese Patent Application Laid-open No. 2009-226087 discloses a method for determining the propriety of the insertion conditions by providing position, angle and speed where the tip of the needle is contacting the surface of the organ, as the insertion conditions, and simulating an error when the needle is inserted from this position at a predetermined angle and predetermined speed.

SUMMARY OF THE INVENTION

The puncture process is considered by dividing the process into three stages: (1) the tip of the needle entered through the skin and reaches the surface of the organ, (2) the tip of the needle presses against the organ and punctures (pierces) the surface of the organ, and (3) the needle enters the organ and reaches the target segment. The above mentioned method according to Japanese Patent Application Laid-open No. 2006-271546 is a method for controlling the path of the needle in stage (3), and the method according to Japanese Patent Application Laid-open No. 2009-226087 is a method for planning the position and angle of the tip of the needle when the tip reaches the surface of the organ in stage (1).

However, through study the present inventor learned that the deformation of the organ in stage (2) has a major influence on puncture error (deviation between the position where the tip of the needle reached and the target segment). In other words, the surface of the organ has a certain strength, hence the organ is deformed by the force received from the tip of the needle during the period from the time when the tip of the needle contacts the surface of the organ to the time when the organ is punctured. Then the needle may bend or the angle of the needle deviates due to the restoring force of the organ, or the target segment (e.g. tumor) deviates from the path of the needle due to the deformation of the organ itself.

If the organ is punctured in a state where the path of the needle and the target segment deviate from each other and the needle enters into the organ, it is difficult to sufficiently correct puncture error by the path correction in stage (3) alone. Moreover, the path correction in stage (3) should be minimal since healthy tissue inside the organ may be damaged. Therefore it is preferable to correct the path of the needle (e.g. angle) during stage (2), that is, before the needle punctures and enters the organ, so as to minimize puncture error due to deformation of the organ.

With the foregoing in view, it is an object of the present invention to provide a technique to plan the puncture operation that can minimize an error generated when the needle is inserted into the organ.

The present invention in its first aspect provides a puncture planning apparatus, comprising:

a simulation unit that simulates movement of an organ and a puncture needle when the puncture needle is inserted toward a target segment inside the organ, by simulation using an organ model; and a planning unit that plans, based on a result of the simulation, how to move a puncture needle when an actual organ is punctured, and outputs a planning result, wherein the simulation unit executes a plurality of times of the simulation of an operation to advance the puncture needle while correcting an angle of the puncture needle so as to follow a movement of the target segment due to deformation of the organ, wherein conditions of an advancement speed of the puncture needle are changed for each of the plurality times of the simulation, and the planning unit performs planning using the best simulation result out of the plurality of simulation results acquired under different conditions of the advancement speed of the puncture needle.

The present invention in its second aspect provides a puncture planning apparatus, comprising:

a simulation unit that simulates movement of an organ and a puncture needle when the puncture needle is inserted toward a target segment inside the organ, by simulation using an organ model; and a planning unit that plans, based on a result of the simulation, how to move a puncture needle when an actual organ is punctured, and outputs a planning result, wherein the simulation unit executes a plurality of times of the simulation of an operation to advance the puncture needle by a first target displacement, while correcting an angle of the puncture needle so that the angle of the puncture needle becomes a first target angle, and then to advance the puncture needle toward the target segment with correcting the angle of the puncture needle so that the angle of the puncture needle becomes a second target angle, wherein conditions of the first target angle and the first target displacement are changed for each of the plurality times of the simulation, and the planning unit performs planning using the best simulation result out of the plurality of simulation results acquired under different conditions of the first target angle and the first target displacement.

The present invention in its third aspect provides a puncture planning apparatus, comprising:

a simulation unit that simulates movement of an organ and a puncture needle when the puncture needle is inserted toward a target segment inside the organ, by simulation using an organ model; and a planning unit that plans, based on a result of the simulation, how to move a puncture needle when an actual organ is punctured, and outputs a planning result, wherein the simulation unit executes a plurality of times of the simulation of an operation to advance the puncture needle until a force that acts on the puncture needle becomes a first target force, while correcting an angle of the puncture needle so that the angle of the puncture needle becomes a first target angle, and then to advance the puncture needle toward the target segment with correcting the angle of the puncture needle so that the angle of the puncture needle becomes a second target angle, wherein conditions of the first target angle and the first target force are changed for each of the plurality times of the simulation, and the planning unit performs planning using the best simulation result out of the plurality of simulation results acquired under different conditions of the first target angle and the first target force.

The present invention in its fifth aspect provides a puncture system, comprising:

the puncture planning apparatus according to the present invention;

a manipulator that has a puncture needle; and a control unit that controls the manipulator based on the planning result acquired by the puncture planning apparatus.

The present invention in its sixth aspect provides a puncture planning method, comprising:

a simulation step of a computer simulating movement of an organ and a puncture needle when the puncture needle is inserted toward a target segment inside the organ, by simulation using an organ model; and a planning step of the computer planning, based on a result of the simulation, how to move a puncture needle when an actual organ is punctured, and outputting a planning result, wherein in the simulation step, a plurality of times of the simulation of an operation to advance the puncture needle while correcting an angle of the puncture needle so as to follow the movement of the target segment due to deformation of the organ is executed, wherein conditions of an advancement speed of the puncture needle are changed for each of the plurality times of the simulation, and in the planning step, planning is performed using the best simulation result out of the plurality of simulation results acquired under different conditions of the advancement speed of the puncture needle.

The present invention in its seventh aspect provides a puncture planning method, comprising:

a simulation step of a computer simulating movement of an organ and a puncture needle when the puncture needle is inserted toward a target segment inside the organ, by simulation using an organ model; and a planning step of the computer planning, based on a result of the simulation, how to move a puncture needle when an actual organ is punctured, and outputting a planning result, wherein in the simulation step, a plurality of times of the simulation of an operation to advance the puncture needle by a first target displacement, while correcting an angle of the puncture needle so that the angle of the puncture needle becomes a first target angle, and then to advance the puncture needle toward the target segment with correcting the angle of the puncture needle so that the angle of the puncture needle becomes a second target angle is executed, wherein conditions of the first target angle and the first target displacement are changed for each of the plurality times of the simulation, and in the planning step, planning is performed using the best simulation result out of the plurality of simulation results acquired under different conditions of the first target angle and the first target displacement.

The present invention in its eighth aspect provides a puncture planning method, comprising:

a simulation step of a computer simulating movement of an organ and a puncture needle when the puncture needle is inserted toward a target segment inside the organ, by simulation using an organ model; and a planning step of the computer planning, based on a result of the simulation, how to move a puncture needle when an actual organ is punctured, and outputting a planning result, wherein in the simulation step, a plurality of times of the simulation of an operation to advance the puncture needle until a force that acts on the puncture needle becomes a first target force, while correcting the angle of the puncture needle so that the angle of the puncture needle becomes a first target angle, and then to advance the puncture needle toward the target segment with correcting the angle of the puncture needle so that the angle of the puncture needle becomes a second target angle is executed, wherein conditions of the first target angle and the first target force are changed for each of the plurality times of the simulation, and in the planning step, planning is performed using the best simulation result out of the plurality of simulation results acquired under different conditions of the first target angle and the first target force.

The present invention in its ninth aspect provides a non-transitory computer readable storage medium, storing a program that causes a computer to execute each of the steps of the puncture planning method according to the present invention.

According to the present invention, the puncture operation that can minimize an error generated when the needle is inserted into the organ can be planned.

Further features of the present invention will become apparent from the following description of exemplary embodiments with reference to the attached drawings.

DESCRIPTION OF THE EMBODIMENTS

The present invention relates to a technique to plan a puncture operation (how to move a puncture needle) to minimize puncture error when the puncture needle is inserted toward a target segment inside an organ. The acquired planning result can be used for outputting guidance to an operator (e.g. physician) performing the puncture, or for controlling a puncture robot. In the following embodiment, an organ model considering viscoelasticity and non-linearity is used, and advancement and rotation of a puncture needle held by a manipulator of a puncture robot are simulated. Then information represented by an angle and advancement displacement (or advancement speed) of the puncture needle in each time step, which is a control response of the robot, is outputted as a planning result.

(System Configuration)

Figure 1:
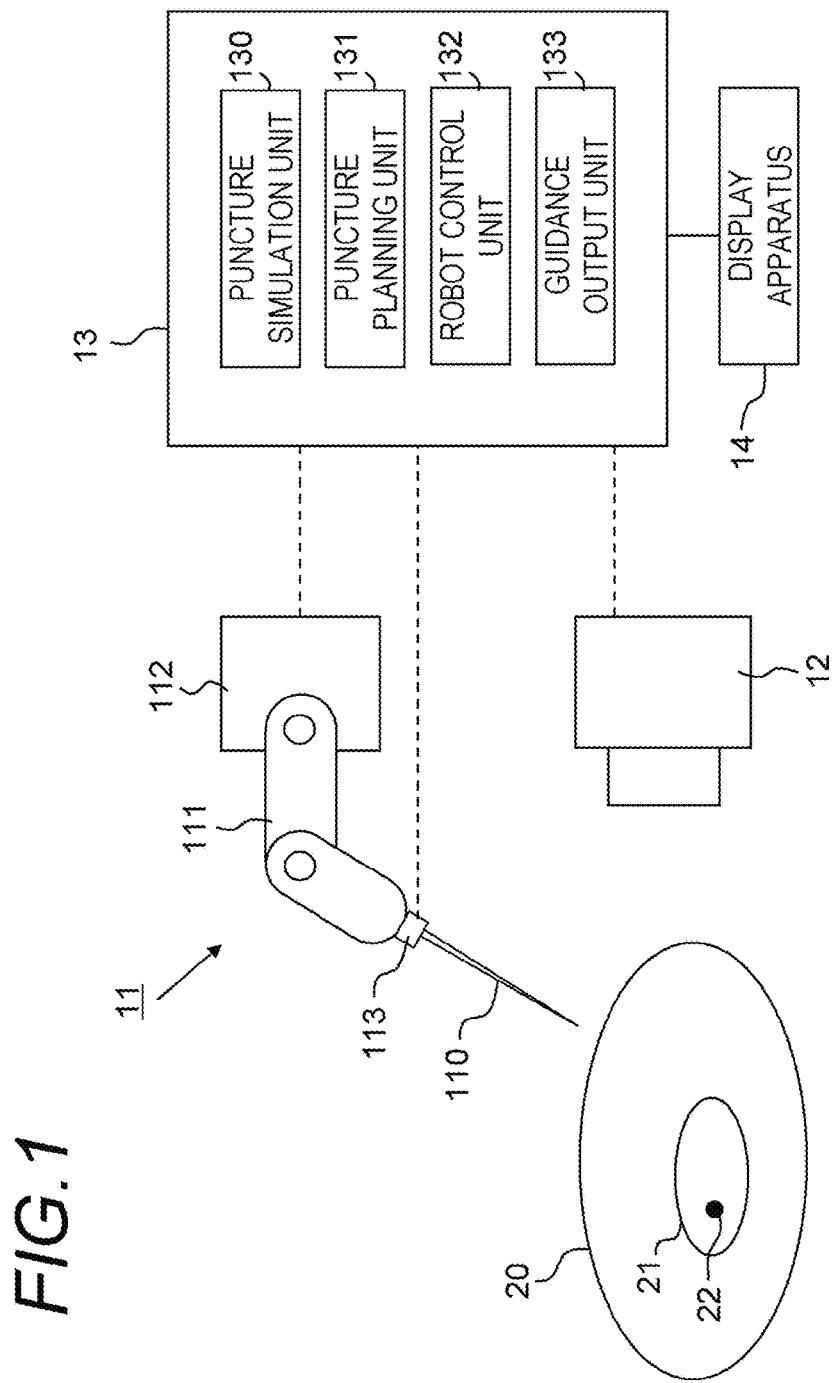
FIG. 1 is a block diagram depicting a configuration of a puncture system according to an embodiment.

FIG. 1 is a schematic diagram depicting a configuration of a puncture system according to the embodiment of the present invention. This puncture system is a system for performing puncture (needle insertion) into an organ 21 of a human 20, and is mainly constituted by a puncture robot 11, an image acquiring apparatus 12, a puncture control apparatus 13 and a display apparatus 14.

The puncture robot 11 has a puncture needle 110, an articulated manipulator 111 that holds the puncture needle 110, an actuator 112 that drives the manipulator 111, and a pressure sensor 113 that detects the reaction force that the puncture needle 110 receives from the puncture target. The puncture needle 110 may include, depending on the intended use, a unit that irradiates a radio wave, a microwave or laser, a unit that collects body fluid, tissue or the like, and a unit that senses physical quantities inside the living body, however none of these are illustrated. It is preferable that the manipulator 111 is controlled such that the puncture needle 110 always passes through the insertion hole on the body surface, and a remote center of motion (RCM) mechanism is used to fix the rotation center of the puncture needle 110 in the angle adjustment.

The image acquiring apparatus 12 is an apparatus to acquire a tomographic image and/or a three-dimensional image of the organ 21. For the image acquiring apparatus 12, an ultrasound diagnostic apparatus, a magnetic resonance imaging (MRI) apparatus or an X-ray apparatus, for example, can be used. The image data acquired by the image acquiring apparatus 12 is used for generating an organ model used for the later mentioned puncture simulation, and outputting image guidance when puncture is actually performed, for example.

The puncture control apparatus 13 has functional components, such as a puncture simulation unit (puncture simulator) 130, a puncture planning unit 131, a robot control unit (robot controller) 132 and a guidance output unit 133. The puncture simulation unit 130 has a function to computer-simulate the movement of an organ 21 and the puncture needle 110 using an organ model when the puncture needle is inserted toward a target segment 22 inside the organ 21. The puncture planning unit 131 has a function to plan how to move the puncture needle 110 when the actual organ 21 is punctured based on the result of the simulation. The robot control unit 132 has a function to control the manipulator 111 based on the planning result acquired by the puncture planning unit 131. The guidance output unit 133 has a function to guide the physician performing puncture how to move the puncture needle 110.

The puncture control apparatus 13 can be constituted by a computer that has hardware resources that include a central processing unit (CPU), a memory, an auxiliary storage apparatus, an input apparatus and an I/F with external apparatuses. The above mentioned functions 130 to 133 are implemented by the CPU executing programs stored in the auxiliary storage apparatus, but part or all of the functions 130 to 133 may be implemented by circuits, such as an application-specific integrated circuit (ASIC). In this embodiment, the puncture control apparatus 13 plays three roles: the puncture planning apparatus, the puncture robot control apparatus and the puncture guiding apparatus, but separate apparatuses may be installed to play these roles respectively.

Usages of the above mentioned puncture system are roughly divided into two: one is the puncture system supporting (assisting) the puncture operation performed by a physician, and the other is the puncture system that automatically executes the puncture operation. In the former case, when the physician inserts the puncture needle 110, for example, the puncture system assists the positioning and angle control of the puncture needle 110 according to the planning result, whereby accurate puncture is easily executed. In this case, it is even better if the operation by the physician is supported by the guidance output unit 133 displaying an image acquired by the image acquiring apparatus 12 on the display apparatus 14, or outputting guidance on how to move the puncture needle 110 (desirable advancement speed, angle or the like) in accordance with the planning result. For example, a guidance to correct deviation between the planning result (ideal movement of the puncture needle) and the actual state of the puncture needle 110 (e.g. "Reduce speed slightly", "Rotate to right slightly") can be outputted. To output guidance, the display apparatus 14 may be used, or voiced guidance or a lit or blinking lamp may be used. In the case of the latter usage, on the other hand, the puncture system automatically inserts the puncture needle 110 in accordance with the planning result. Manual operation is basically unnecessary, and all that is required of the physician is to merely check whether puncture is correctly being executed via an image acquired by the image acquiring apparatus 12 or the like.

Embodiment 1

Functions of the puncture simulation unit 130 and the puncture planning unit 131 of the puncture control apparatus 13 will now be described in detail.

(Puncture Simulation and Planning)

Figure 2:
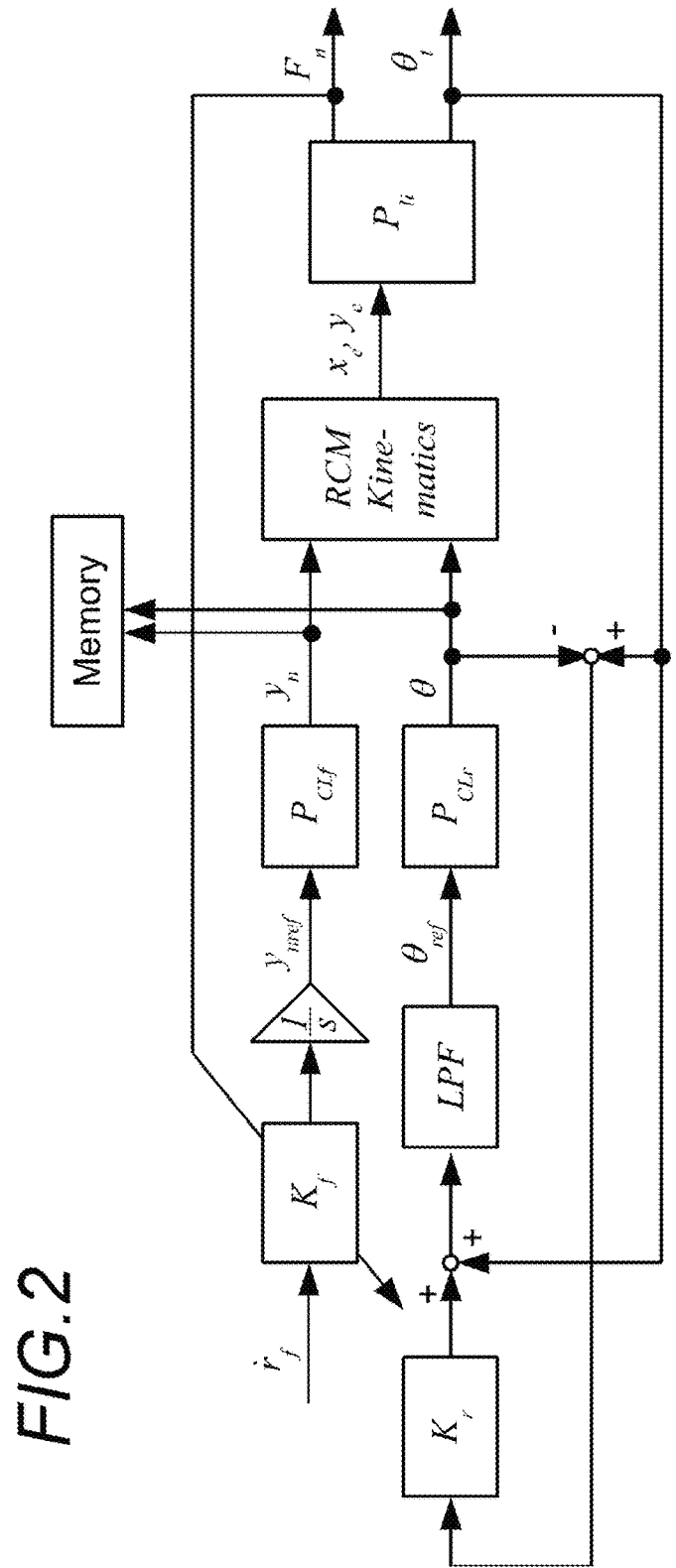
FIG. 2 is a block diagram depicting a control system used for puncture simulation according to Embodiment 1.

FIG. 2 is a block diagram depicting a control system of a puncture robot used for the puncture simulation.

Here $P_{li}$ is a model of an organ (liver in this embodiment). $P_{CLf}$ is a model of a servo system to move the needle held by the robot forward or backward, and has an internal feedback loop to follow the movement of the needle based on a needle advancement target displacement $y_{nref}$ as a reference signal, and the control output thereof becomes the needle advancement displacement $y_n$. The control system is further characterized in that the needle advancement speed is continuously changed in accordance with the puncture reaction force $F_n$ in order to improve the puncture accuracy. The puncture reaction force refers to the reaction force that the puncture needle receives when the puncture needle presses an organ or the like. The needle advancement target displacement $y_{nref}$ is generated by multiplying the needle advancement target speed $r_f$ which is freely set as an initial value, by a needle advancement speed gain $K_f$, which changes with the puncture reaction force $F_n$ as a parameter, and integrating this signal.

$P_{CLr}$ is a servo system that controls the angle (orientation) of the needle, and has an internal feedback loop that follows the needle target angle $\theta_{ref}$ as the reference signal, and the control output thereof becomes the needle angle $\theta$. $\theta_t$ is a target angle, and is an angle of a line connecting the rotation center of the needle and the target segment (target) inside the organ. If the target angle $\theta_t$ is inputted to $P_{CLr}$, the puncture needle precisely follows the movement of the target segment, but the frequency bands of a robot or an individual holding the puncture needle are actually limited. Therefore these frequency bands are modeled as low pass filters LPFs. Further, a feedback loop using a compensator $K_r$, including an integration characteristic to compensate for steady-state deviation, is disposed.

By this configuration, operation to advance the puncture needle, while correcting the angle of the puncture needle so as to follow the movement of the target segment due to the deformation of the organ, can be simulated. The puncture simulation unit 130 executes a plurality of times of puncture simulation while changing the needle advancement speed gain $K_f$, which is a condition of the advancement speed of the puncture needle, and stores the simulation result acquired under each condition in a memory. The simulation result is stored in a time series data format, for example, that indicates values of the needle advancement displacement $y_n$ and the needle angle $\theta$ in each time step.

If a condition of the advancement speed of the puncture needle is changed, the puncture error and the puncture time become different. Therefore the puncture planning unit 131 selects the best simulation result out of the plurality of simulation results acquired under different conditions, and performs puncture planning based on the selected simulation result. For example, the simulation result, in which the puncture error (error of needle angle with respect to target segment) at the point when the puncture needle punctures the organ is the minimum, is selected as the best simulation result. If there are a plurality of simulation results in which the puncture error at the point when the puncture is generated is within a predetermined range (tolerance), the simulation result in which time required for puncture is shortest may be selected as the best simulation result. This is because the burden on a patient is lighter as the puncture processing time is shorter. It is also preferable that the simulation result, in which both the puncture error when the puncture is generated and the maximum value of the puncture error after the puncture needle contacts the organ are within tolerance, is selected as the best simulation result. This is because the time required for puncture can be decreased, and the risk of damaging healthy tissue can be lessened by not only minimizing ultimate puncture error, but also minimizing error in the middle of insertion.

The control system used for modeling and simulation of the organ and the robot will be described in detail, and the planning result acquired by the simulation will be shown below.

1) Modeling

Figure 3:
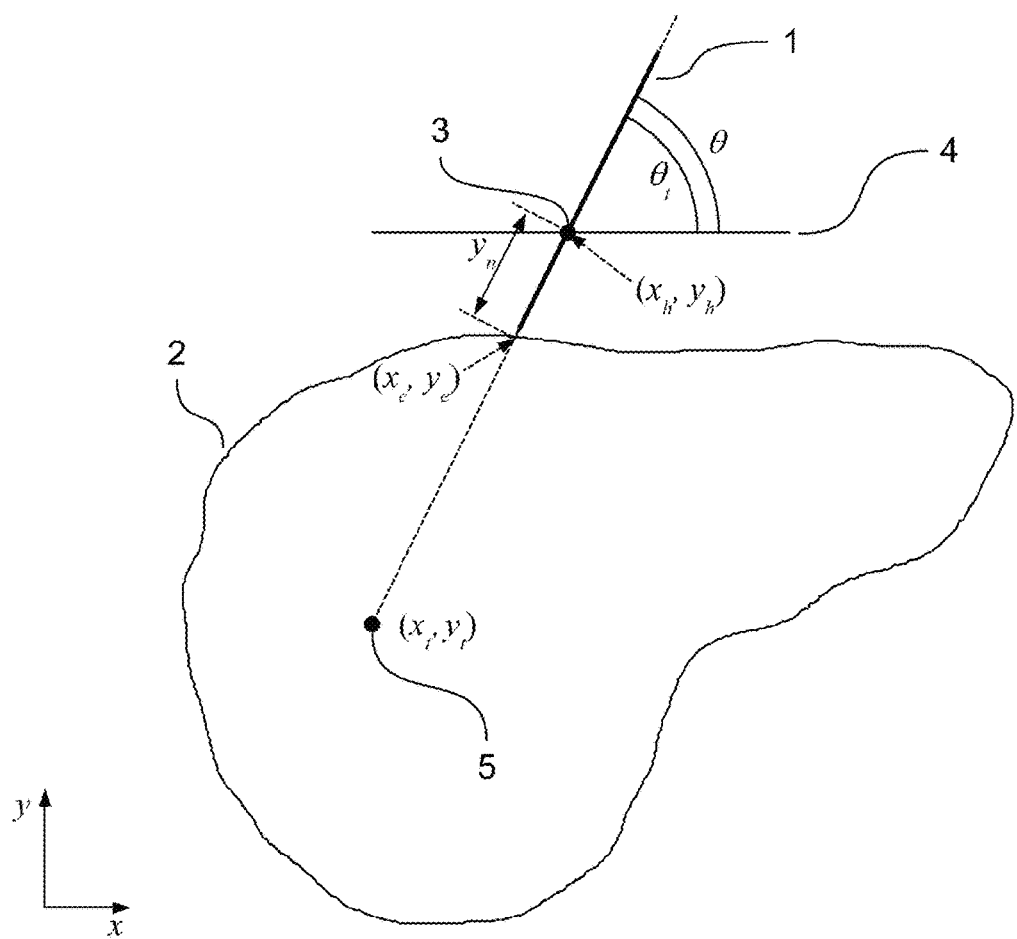
FIG. 3 is a diagram depicting a model of an organ and a puncture needle used for puncture simulation.

FIG. 3 shows an overview of a model that is used for simulation in this embodiment. 1 is a drivable puncture needle, and is held by a manipulator, which is not illustrated. As mentioned above, it is preferable that the manipulator is controlled such that the puncture needle 1 always passes through the insertion point 3 ($x_h$, $y_h$) on the body surface 4, for which an RCM mechanism may be used. In this embodiment, $\theta$ is the angle of the puncture needle 1 with respect to the x axis. 2 indicates the organ, and 5 indicates the puncture target segment (target). $\theta_t$ is an angle of the line connecting the puncture target segment 5 and the insertion point 3 (rotation center of the puncture needle 1) with respect to the x axis. In this embodiment, the distance of advancement of the puncture needle 1 is defined as $y_n$. Thereby the coordinate of the needle tip ($x_e$, $y_e$) becomes $$x_e = x_h - y_n \cos\theta, y_e = y_h - y_n \sin\theta \quad (1)$$

The organ 2 is modeled using a finite element method. In this embodiment, the method disclosed in Japanese Patent Application Laid-open No. 2009-226087 is used. According to Japanese Patent Application Laid-open No. 2009-226087, the finite element model of the organ having viscoelasticity is represented by $$K(U)D^k U = F \quad (2)$$

where K is a combined rigidity matrix, U is a displacement vector, $D^k$ is a k-th order fractional differentiation operator, and F is an external force vector. Here the rigidity matrix has non-linearity where U is a variable. The rigidity matrix of the m-th element, which is $K_m(\varepsilon)$, is given by $$K_m(\varepsilon) = \begin{cases} K_{m0} & (\varepsilon < \varepsilon_0) \\ \{1 + \alpha_\varepsilon(\varepsilon - \varepsilon_0)^2\}K_{m0} & (\varepsilon > \varepsilon_0) \end{cases} \quad (3)$$

where $\alpha_\varepsilon$ is a coefficient that indicates an increase in elasticity respectively, $\varepsilon$ is a strain, and $\varepsilon_0$ is a strain when the elasticity starts to change. When $K_{m0}$ is an element rigidity matrix in an area that is linear with respect to the strain, t is a plate thickness of the triangular element, $\Delta$ is a surface area of the triangular element, B is a strain-displacement matrix, and D is a stress-strain matrix, then $$K_{m0} = t\Delta B^T DB \quad (4)$$

is established.

The model of the organ is generated from an image of the organ of the patient acquired by the image acquiring apparatus 12 or the like. In this case, it is also preferable to set the rigidity matrix of the organ using the attribute information, such as age, gender and race of the patient, and information acquired by different diagnosis and measurement. By using the organ model of the patient, reliability of the simulation can be improved.

2) Control System Design

Figure 4:
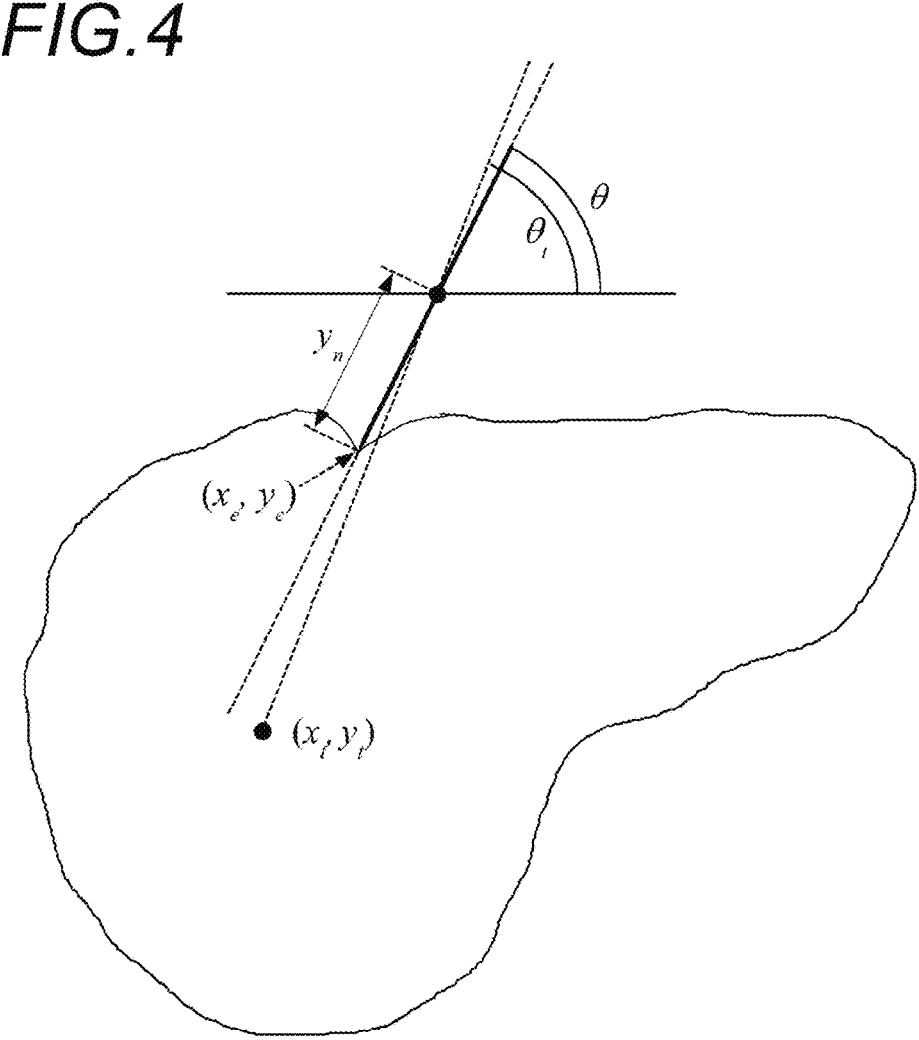
FIG. 4 is a diagram depicting deviation of a target segment due to deformation of the organ.

In order to reach the puncture target segment 5 without error, the angle $\theta$ is set such that the puncture target segment 5 is located on an extended line of the puncture needle 1, then puncture is started. However as shown in FIG. 4, the organ deforms as the needle advances, whereby the puncture target segment deviates from the extended line of the puncture needle.

In this embodiment, simulation is executed using the organ model in order to reach the puncture target segment without error, and planning is performed so that the angle $\theta$ of the puncture needle 1 properly adjusted as the puncture needle advances. For this, the robot is controlled such that puncture error is minimized in the simulation. The angle $\theta$ and the needle advancement displacement $y_n$ in each time step, which are control responses of the robot, become the result of the planning.

To minimize puncture error, it is preferable that the angle θ of the puncture needle is always controlled to $$\theta = \theta_t \quad (5)$$

However the robot to hold the puncture needle has a frequency band, hence simulation considering the controllability of the robot must be executed. In this embodiment, the control system shown in the block diagram in FIG. 2 is constructed. Here $P_{li}$ is a model of a liver, $P_{CLf}$ is a model of a servo system to move the needle held by the robot forward or backward, and has an internal feedback loop to follow the movement of the needle based on a needle advancement target displacement $y_{nref}$ as a reference signal, and the control output thereof becomes the needle advancement displacement $y_n$. $P_{CLr}$ is also a servo system to control the angle of the robot holding the needle, and has an internal feedback loop that follows the movement of the needle based on a needle target angle $\theta_{ref}$ as a reference signal, and the control output thereof becomes the needle angle θ. Further, the frequency characteristic of the robot is modeled as a low pass filter LPF. However, if the angle target value is used for this model as the angle $\theta_t$ of the puncture target segment, a steady-state deviation is generated between the angle θ of the puncture needle and the angle $\theta_t$ of the puncture target segment. In order to compensate for this steady-state deviation, a compensator $K_r$ that includes the integration characteristic is used in this embodiment, and a feedback loop where the input of the compensator $K_r$ is the puncture angle error $\theta_e$ between the angle θ of the puncture needle and the target angle $\theta_t$ of the puncture target segment, is created. The puncture angle error $\theta_e$ is given by the following expression.

$$\theta_e = \theta - \theta_t \quad (6)$$

With the above mentioned configuration, simulation to control the angle while advancing the puncture needle and acquire a highly accurate puncture planning result becomes possible. In this embodiment, the needle advancement speed is continuously changed in accordance with the puncture reaction force $F_n$, in order to further improve puncture accuracy. In a state where the needle advances and tissue is easily punctured, the strain of the organ increases as shown by Expression (3), and elasticity changes. This change in elasticity generates a major puncture angle error. If the needle advancement speed is constant at this time, the tissue is punctured without taking sufficient time to compensate for puncture angle error, and as a result, a major puncture error is generated. To prevent this, the needle advancement target speed $r_f$ is multiplied by a needle advancement speed gain $K_f$, which changes with the puncture reaction force as a parameter, and the result is integrated to generate the needle advancement target displacement. Thereby the needle advancement speed can be continuously reduced as the puncture reaction force increases.

Figure 5:
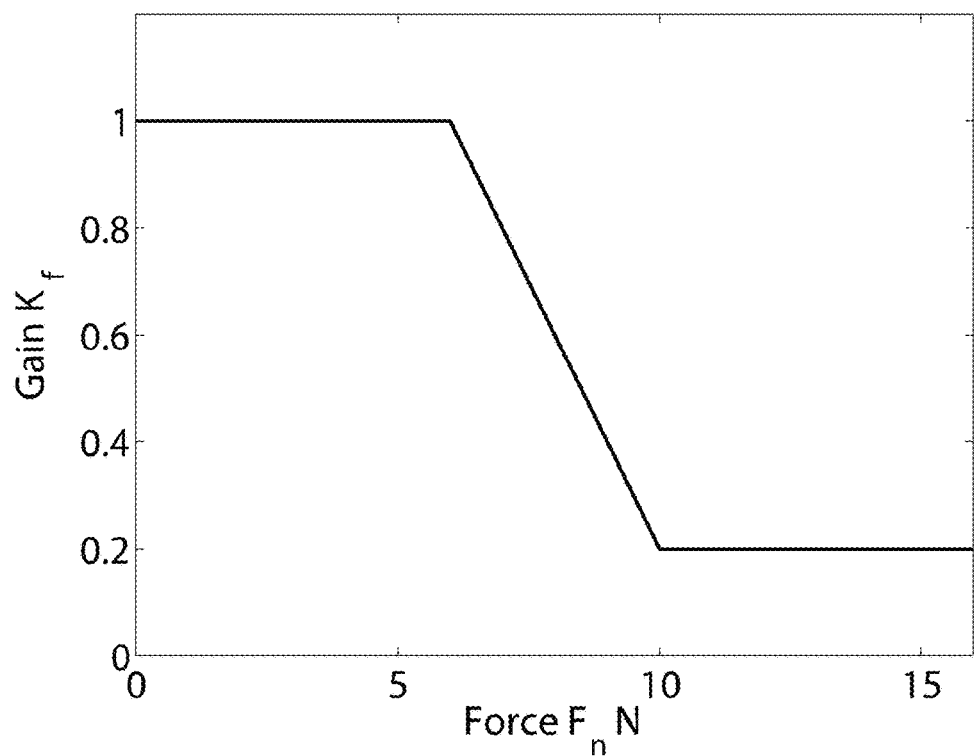
FIG. 5 shows a parameter change of the control system in the puncture simulation.

In this embodiment, the gain $K_f$ is changed in accordance with the puncture reaction force $F_n$, as shown in FIG. 5. The gain $K_f$ is 1 when the puncture reaction force is the reaction force threshold $F_{nmin}$ or less, hence the puncture needle advances at a predetermined speed. When the puncture reaction force is the reaction force threshold $F_{min}$ or more, the gain $K_f$ is decreased at a predetermined reduction rate which is expressed as a linear function of the inclination $a_k$. $K_{fmin}$ is predetermined as the minimum value of the gain $K_f$. As a result, the gain $K_f$ becomes $$K_f = 1 (F_n \leq F_{nmin}) \quad (7)$$

$$K_f = a_k F_n - a_k F_{nmin} + 1 \left( F_{nmin} < F_n < \frac{a_k F_{nmin} - 1 + K_{fmin}}{a_k} \right) \quad (8)$$

$$K_f = K_{fmin} \left( F_n \geq \frac{a_k F_{nmin} - 1 + K_{fmin}}{a_k} \right) \quad (9)$$

Here the parameter $a_k$ is a parameter to adjust the reduction rate of the needle advancement speed.

In the example in FIG. 5, the reaction force threshold $F_{nmin}$ is set to 6N, and the minimum value of the gain $K_{fmin}$ is set to 0.2, but these values may be changed depending on the organ model (depending on the patient or depending on the type of organ).

3) Simulation

The result of the simulation using the control system described above will be shown. In this embodiment, Expression (2) is incrementally transformed, and non-linear rigidity is computed using the Newton-Raphson method, and viscoelasticity is computed using the sampling scaling properties.

Figure 6A:
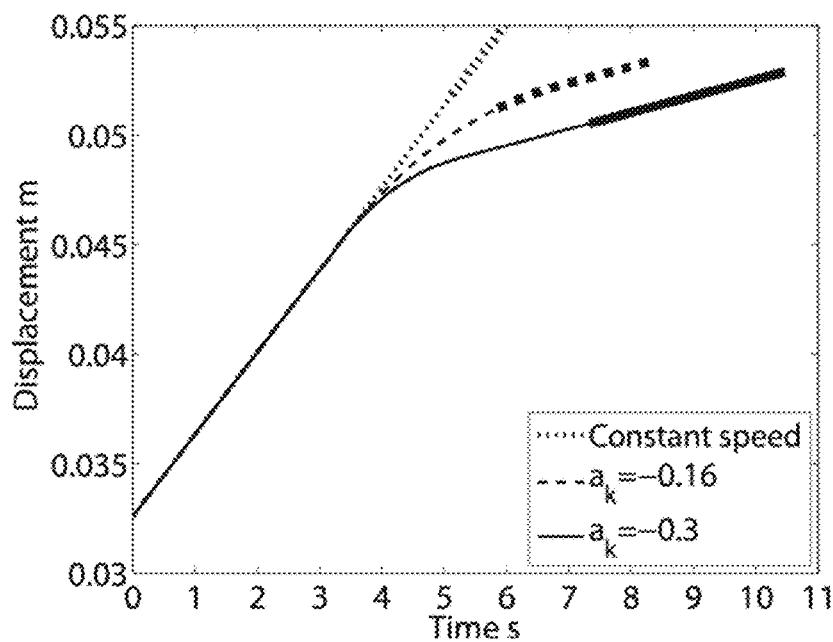
FIG. 6A to FIG. 6D each show the result of the simulation of Embodiment 1.
Figure 6B:
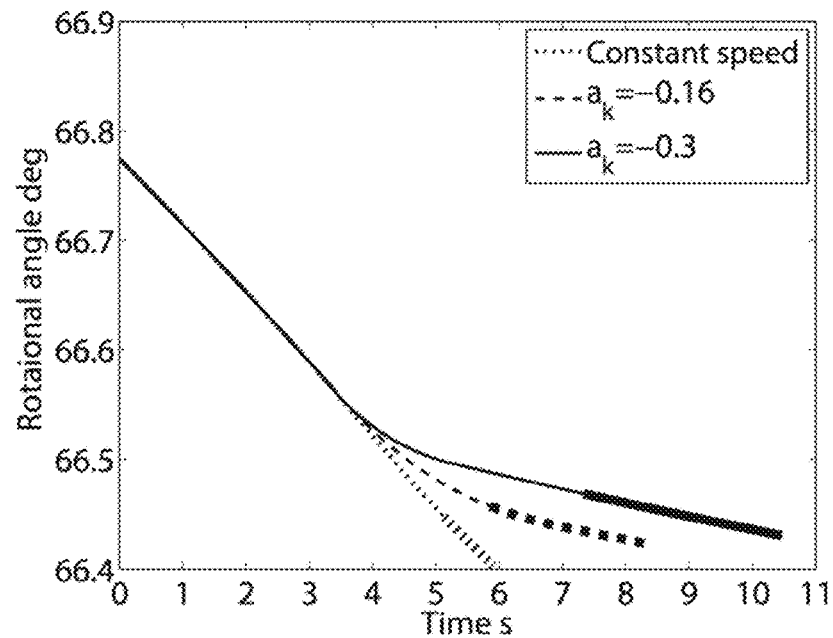
Figure 6C:
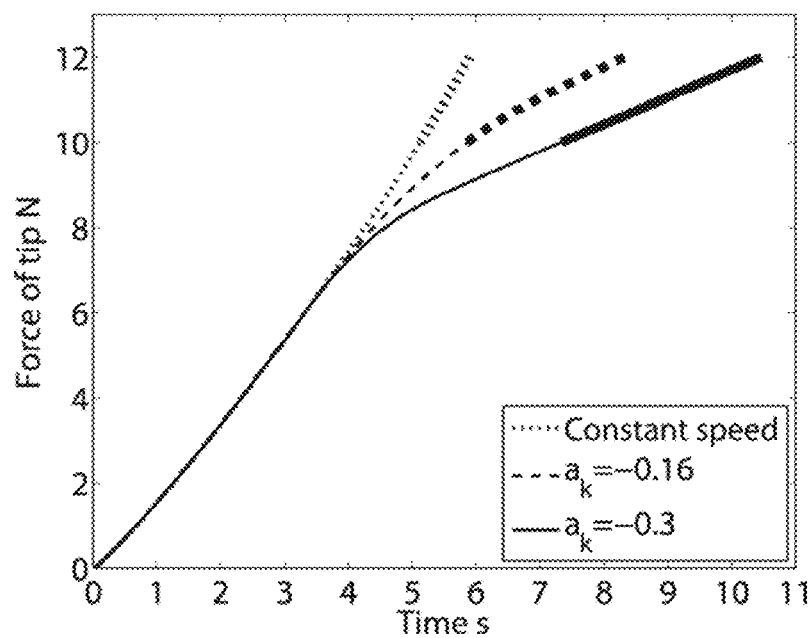
Figure 6D:
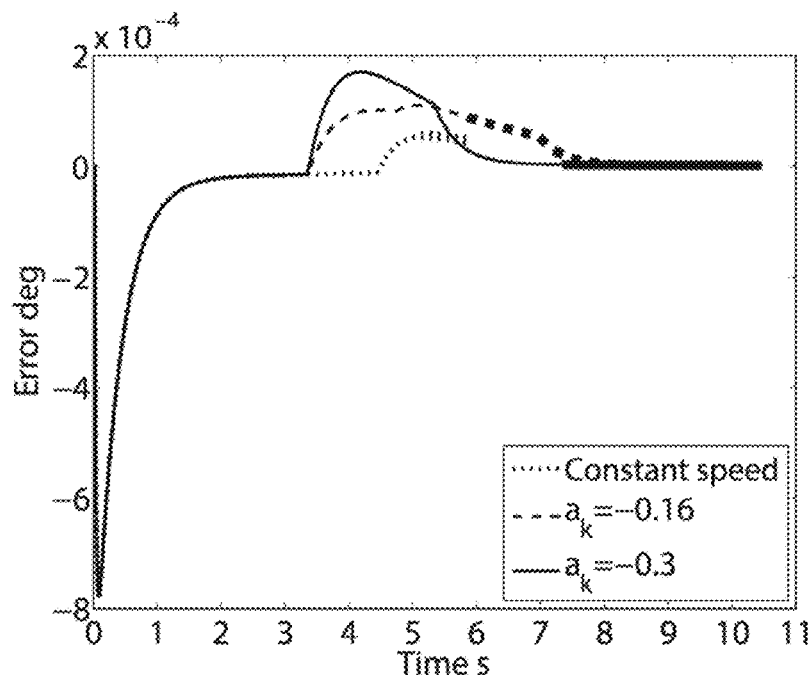

FIG. 6A shows the advancement displacement of the puncture needle, FIG. 6B shows an angle of the puncture needle, FIG. 6C shows the reaction force received by the tip of the puncture needle, and FIG. 6D shows the puncture angle error. The abscissa is elapsed time. The result when the inclination $a_k$ is set to −0.3 is indicated by the solid line, the result when the inclination $a_k$ is set to −0.16 is indicated by the broken line, and for comparison, the result when the advancement speed is constant is indicated by the dotted line. In this embodiment, assuming that the tissue at the tip of the needle is punctured (or that the possibility of puncture generation increases) when the puncture reaction force is 10N or more, the time zone is plotted as a bold line. The value of this reaction force (10N) is hereafter called "puncture generating reaction force". The reaction force threshold $F_{nmin}$, to start reducing the needle advancement speed, is 6N. The reaction force threshold $F_{nmin}$ is a threshold to determine whether the puncture needle began to contact the surface of the organ.

As shown in FIG. 6A, in the puncture control of this embodiment (see the solid line and broken line), the speed starts to reduce if the puncture reaction force exceeds the reaction force threshold $F_{nmin}$ (that is, if it is determined that the puncture needle contacted the organ), therefore the change in the advancement displacement becomes gentle. If the organ deforms due to pressing by the puncture needle as shown in FIG. 6B, the puncture target segment moves in the −y axis direction in FIG. 2. Therefore the control system of this embodiment decreases the puncture angle to move the puncture needle in the counterclockwise direction, so as to follow the puncture target segment. FIG. 6C shows that the puncture reaction force increases as the puncture needle advances.

As shown in FIG. 6D, in the result when the inclination $a_k$ is set to −0.3 (solid line), the puncture angle error becomes sufficiently small in the time zone when the puncture reaction force is 10N or more (about 7.2 seconds or later plotted by the bold line). In other words, the puncture angle error has been sufficiently compensated for before the organ is punctured. In comparison, in the case of conventional control where the advancement speed is constant (dotted line), the rigidity of the organ changes at around 4.5 seconds, whereby the puncture error is generated. Then the puncture reaction force becomes the puncture generating reaction force before sufficiently compensating for error, since the needle advancement speed is constant. Because of this, tissue is easily punctured by the tip of the needle in the state where puncture error remains. In the result, when the inclination $a_k$ is set to −0.16 (broken line), a puncture angle error is generated by the start of needle advancement speed reduction at around 3.4 seconds. The puncture error further increases since the rigidity of the organ changes at around 5.5 seconds. Thereafter puncture error can be compensated for by controlling the angle of the needle, since the needle advancement speed is low, but the puncture angle error in the time zone when the puncture reaction force exceeds the puncture generating reaction force becomes larger than the result of control to keep the needle advancement speed constant, as indicated by the dotted line.

In the case of the result when the inclination $a_k$ is set to −0.3 (solid line), the puncture angle error becomes high at around 3.4 seconds because of the start of the needle advancement speed reduction. This error is larger than the error in the result when $a_k$ is −0.16, since the speed reduction is large. However, thereafter the puncture angle error due to the change in the rigidity of the organ hardly increases, since the advancement speed becomes sufficiently low. Then the puncture reaction force exceeds the puncture generating reaction force in a state where the puncture angle error has been sufficiently compensated for, therefore a highly accurate puncture with little error is performed.

As described above, the puncture angle error in the period from when the needle contacts the organ to when a puncture is generated changes if conditions to reduce the needle advancement speed change. Further, as shown in FIG. 6D, the condition of setting the inclination $a_k$ to −0.3 generates a better result than the condition of keeping the advancement speed constant (conventional method), or the condition of setting the inclination $a_k$ to −0.16. This does not mean that the condition of setting the inclination $a_k$ to −0.3 is the optimum. Under this condition of setting the inclination $a_k$ to −0.3, time when the needle advancement speed is lowest increases, and the total puncture time becomes long. Since the puncture error is already sufficiently small at 6 seconds or later, the puncture time could be shorter by decreasing the time zone when the needle advancement speed is lowest.

Therefore in this embodiment, an optimum value of the inclination $a_k$ is searched. In concrete terms, a plurality of times of the puncture simulation is executed while changing the inclination $a_k$ in 0.01 steps at a time, from −0.1 to −0.3, and the inclination $a_k$, when the best result is acquired, is selected. For an index to evaluate the propriety of the inclination $a_k$, various indexes can be used, such as: a puncture error that remains when puncture is generated; a time required for puncture; and a maximum value of puncture errors after the needle started to contact the organ, also a plurality of evaluation indexes may be combined.

Figure 7A:
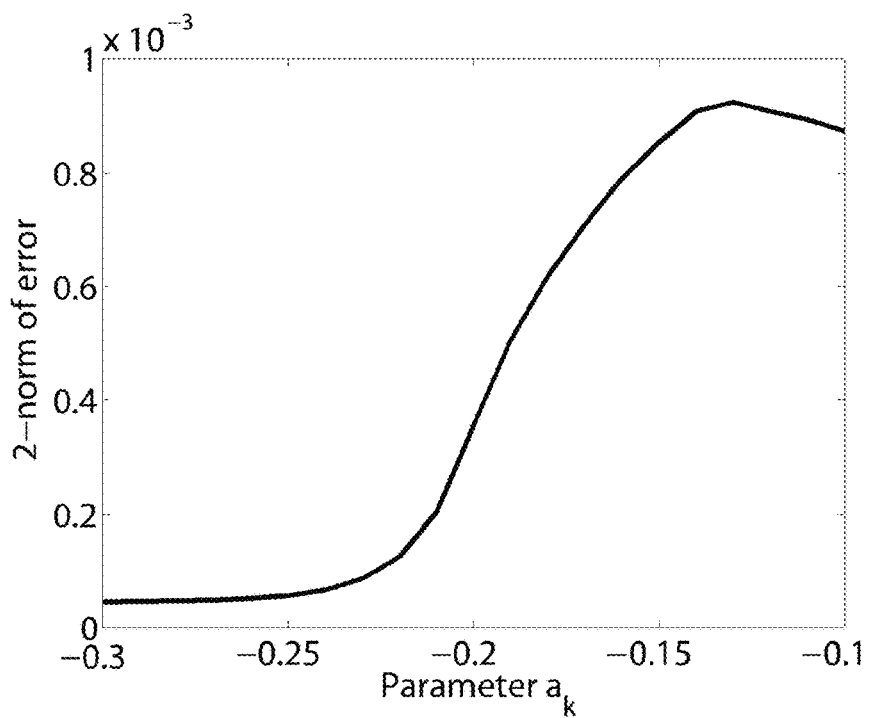
FIG. 7A and FIG. 7B each show the result of the simulation of Embodiment 1.
Figure 7B:
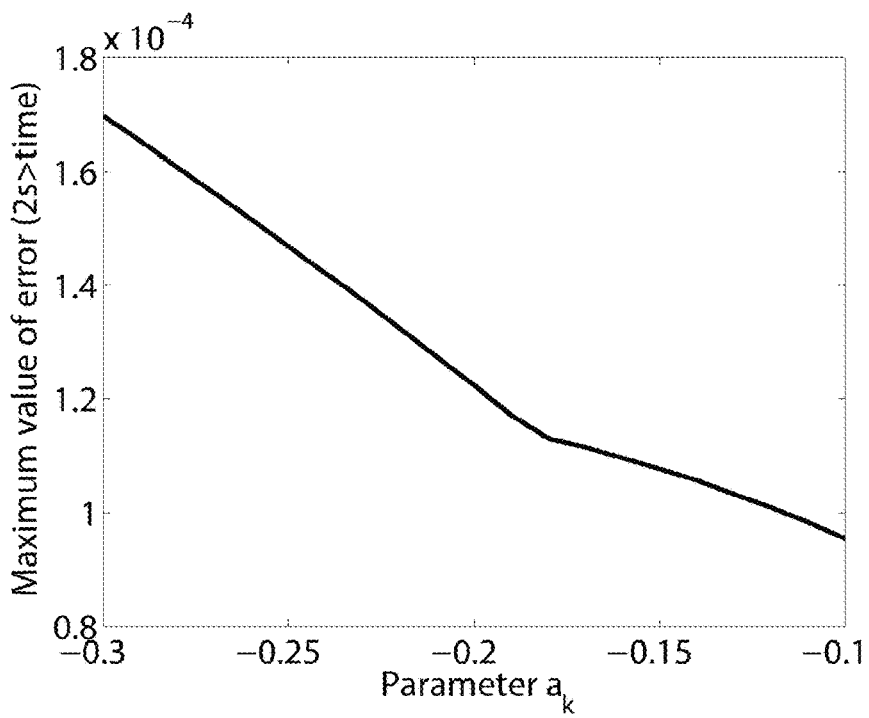

This embodiment uses, as an example, two evaluation indexes: the 2-norm of the puncture angle error in the time zone where the puncture reaction force becomes the puncture generating reaction force; and the maximum value of the puncture angle error after the needle started to contact the organ. FIG. 7A shows the change in the 2-norm of the puncture angle error with respect to the change of the inclination $a_k$, and FIG. 7B shows the change of the maximum value of the puncture angle error with respect to the change of the inclination $a_k$. In FIG. 7B, the maximum values of the puncture angle errors at 2 seconds or later were plotted, since determining a strict contact timing of the needle and organ is unnecessary.

As FIG. 7A shows, the needle advancement speed more quickly reduces after the puncture reaction force exceeds the reaction force threshold $F_{nmin}$ as the absolute value of the inclination $a_k$ is greater, hence error in the time zone when the puncture reaction force becomes the puncture generating reaction force becomes small. However, as the absolute value of the inclination $a_k$ is greater, the velocity change becomes greater, and the puncture error when the velocity changes, which appears at 3 to 4 seconds in FIG. 6D for example, becomes large. Therefore in this embodiment, the 2-norm of the puncture angle error and the puncture error when the velocity changes are both considered, and the inclination $a_k$, with which both values are confined within the predetermined range (tolerance), is selected. If there is a plurality of conditions under which the inclination $a_k$ is confined within the tolerance, a condition of which the 2-norm of the puncture angle error is the smallest therein can be selected. In this embodiment, $a_k=-0.24$ is selected as an optimum value.

Figure 8:
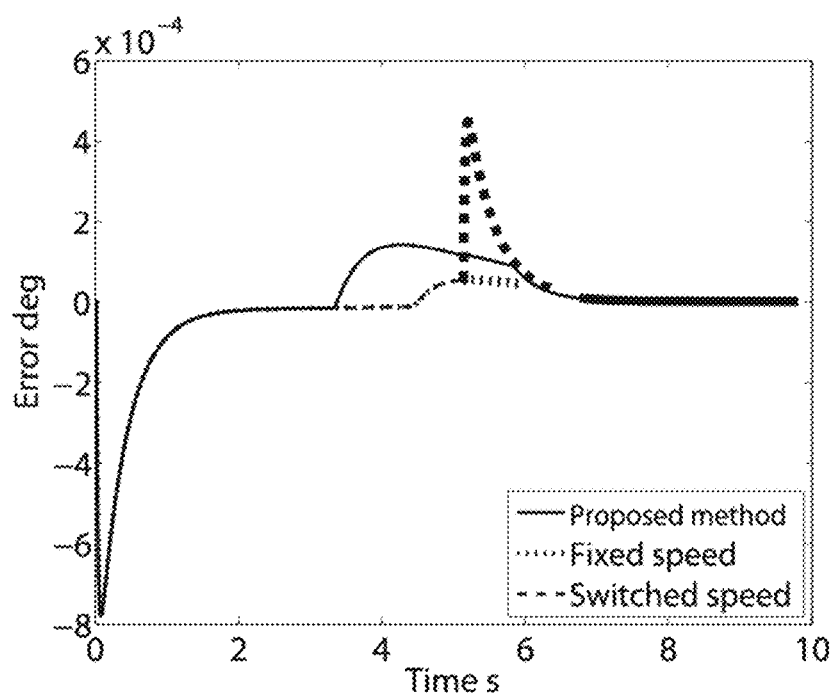
FIG. 8 shows the result of the simulation of Embodiment 1.

In FIG. 8, a puncture error, when the inclination $a_k$ is set to an optimum value using the technique proposed in this embodiment, is indicated by the solid line. As a comparative example, an error due to conventional puncture with constant speed is indicated by the dotted line, and a puncture error when the control to switch the needle advancement speed to low speed is performed when the puncture reaction force reaches the puncture generating reaction force is indicated by the broken line. Just like FIG. 6D, the time zone when the puncture reaction force becomes the puncture generating reaction force is plotted by the bold line. In the case of the proposed technique (solid line), puncture error is minimized in the time zone when the puncture reaction force becomes the puncture generating reaction force, and the puncture time is also reduced by setting the inclination $a_k$ to an optimum value. In the case of the control to switch the speed when the puncture reaction force reaches the puncture generating reaction force (broken line), on the other hand, a major puncture error is generated by the non-linearity of the organ rigidity immediately after switching the speed.

As described above, according to this embodiment, a plurality of times of simulation to control the needle angle and the needle advancement speed is executed with changing the conditions of the needle advancement speed so as to follow the movement of the target segment due to deformation of the organ, and an optimum value of the needle advancement speed condition is determined from the result. Since the puncture planning is performed based on this simulation result, a highly accurate puncture operation with little puncture error can be implemented. Furthermore, according to this embodiment, deformation of the organ is simulated using the organ model considering viscoelasticity and non-linearity, therefore even more accurate planning becomes possible.

Particularly in this embodiment, the speed adjustment is performed to reduce the needle advancement speed in accordance with the puncture reaction force, hence even if the organ is deformed by the pressing force of the puncture needle and the target segment is moved, substantial time for the needle angle to follow the target segment can be taken, whereby the puncture error can be corrected. Also the puncture error can be sufficiently small before the puncture needle punctures the surface of the organ and enters the organ. Since the puncture error should not change very much once an organ is punctured, it is easier to allow the tip of the needle to reach the target segment accurately if the puncture error has been corrected before the organ is punctured. Moreover, path correction after the needle enters the organ can be minimized, which reduces the risk of damage the healthy tissue inside the organ.

The configuration of this embodiment described above is merely an example of the present invention, and is not intended to limit the scope of the present invention to this configuration. For example, according to this embodiment, the inclination $a_k$ is changed as the condition of the needle advancement speed, but any parameter may be changed if a parameter can determine the reduction rate of the needle advancement speed. Further, according to this embodiment, the speed is reduced at a constant reduction rate with respect to the puncture reaction force, but the reduction rate may be changed in accordance with the puncture reaction force. In other words, it is sufficient if the needle advancement speed can be continuously changed in accordance with the puncture reaction force.

Embodiment 2

Figure 9A:
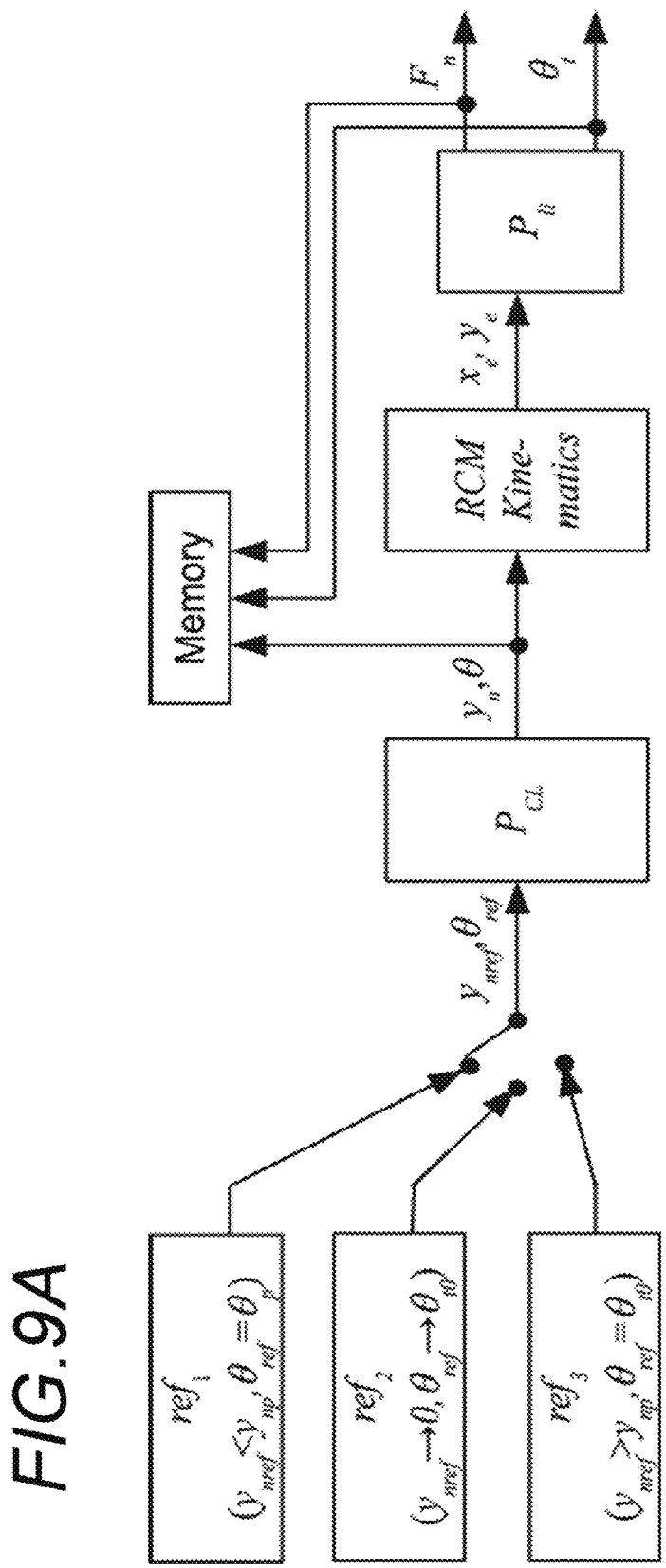
FIG. 9A and FIG. 9B are block diagrams each depicting a control system used for puncture simulation according to Embodiment 2.

FIG. 9A shows a block diagram depicting a control system of a puncture robot used for the puncture simulation, as another embodiment of the functions of the puncture simulation unit 130 and the puncture planning unit 131 of the puncture control apparatus 13. Here, just like Embodiment 1, $P_{li}$ is a model of an organ (liver in this embodiment). $P_{CL}$ has the models $P_{CLf}$ and $P_{CLr}$ of the servo system of Embodiment 1, which are combined in parallel. $P_{CL}$ has an internal feedback loop that follows the needle advancement target displacement $y_{nref}$ and the needle target angle $\theta_{ref}$ as the reference signals. The control outputs of $P_{CL}$ become the needle advancement displacement $y_n$ and the needle angle $\theta$. Just like embodiment 1, $F_n$ denotes the puncture reaction force, and $\theta_t$ denotes the target angle.

In this embodiment, the simulation is performed using a control system that has three types of reference signals: $ref_1$, $ref_2$ and $ref_3$, for the needle advancement displacement and the needle angle. The control system has a switching unit to switch the reference signal in accordance with the time. In this embodiment, the angle when the puncture needle 110 is parallel with the line connecting the insertion point (rotation center of the puncture needle 110) and the target (target segment) is defined as the initial target angle (second target angle) $\theta_{t0}$. The reference signal $ref_1$ is a signal to perform preparative puncture at angle $\theta_p$ which is different from the initial target angle $\theta_{t0}$ before actually puncturing the target. In this embodiment, this preparative puncture is called "preliminary puncture" or "shift compensation puncture", and the angle $\theta_p$ is called "shift compensation puncture angle" (first target angle). The shift compensation puncture is puncture performed for shifting the target, and is preferably performed not to puncture the organ (with the insertion amount with which the tip of the needle does not reach the organ). Here the needle advancement displacement, with which the organ is not punctured, is defined as the shift compensation puncture displacement $y_{np}$. The reference signal $ref_2$ is a reference signal to allow the shift compensation puncture to transit to the target puncture, return the needle advancement displacement to 0, and rotate the needle angle to the initial target angle $\theta_{t0}$ at the same time. The reference signal $ref_3$ is a reference signal to set the needle angle to the initial target angle $\theta_{t0}$ and advance the needle. According to the technique of this embodiment, the shift compensation puncture is performed based on the reference signals $ref_1$ and $ref_2$, whereby the puncture error shown in Expression (6) can be minimized when the target is punctured based on the reference signal $ref_3$.

By this configuration, the simulation of the shift compensation puncture operation, to compensate for the movement of the target due to deformation of the organ, can be performed. The puncture simulation unit 130 executes a plurality of times of puncture simulation while changing the shift compensation puncture angle $\theta_p$ and the shift compensation puncture displacement $y_{np}$, and stores the simulation result acquired under each condition in the memory. The simulation result is stored in the format of the time series data, for example, which indicates the values of the needle advancement displacement $y_n$ and the needle angle $\theta$ in each time step. Just like Embodiment 1, the puncture planning unit 131 selects the best simulation result out of the plurality of simulation results acquired under different conditions, and performs puncture planning based on the selected simulation result.

To output guidance to correct deviation between the planning result and the actual state of the puncture needle 110, the display apparatus 14 or a voice guidance may be used, just like Embodiment 1. Further, in the control method of this embodiment, a V-shaped instrument that can physical fix the puncture needle at the initial target angle $\theta_{t0}$ and the shift compensation puncture angle $\theta_p$ may be used.

A control system used for modeling and simulation of the organ and the robot will be described in detail, and the planning result acquired by the simulation will be shown below.

1) Modeling

For modeling, a model the same as Embodiment 1 is used.

2) Control System Design

In this embodiment, simulation is performed using the organ model, and the control system, and planning, including the shift compensation puncture, is performed in order to reach the puncture target segment without error. For this, the robot is controlled such that puncture error is minimized in the simulation. Just like Embodiment 1, the angle $\theta$ and the needle advancement displacement $y_n$ in each time step, which are the control responses of the robot, become the result of the planning. FIG. 9A shows a block diagram of the control system of the puncture robot that is used for the puncture simulation.

In the control system of this embodiment, before the puncture toward the target (puncture to advance the needle toward the target), puncture is performed at a first target angle $\theta_p$, which is different from the initial target angle (second target angle). This puncture is a preparative puncture, and in this embodiment, this puncture is called "shift compensation puncture", and the angle $\theta_p$ of the shift compensation puncture is called "shift compensation puncture angle". In the shift compensation puncture, it is preferable that the organ is not punctured, and the needle advancement displacement of the organ is defined as shift compensation puncture displacement $y_{np}$. The reference signal $ref_1$ is a reference signal for the shift compensation puncture. The reference signal $ref_2$ is a reference signal to allow the shift compensation puncture to transit to target puncture, return the needle advancement displacement to 0, and rotate the needle angle to the initial target angle $\theta_{t0}$ at the same time. The reference signal $ref_3$ is a reference signal to set the needle angle to the initial target angle, and advance the needle to the target. By the shift compensation puncture, the puncture error shown in Expression (6) can be minimized. Switching from reference signal $ref_1$ to $ref_2$, or switching from $ref_2$ to $ref_3$, is performed by the switching unit. The switching timing of the reference signals are provided as a parameter of the simulation.

Figure 10:
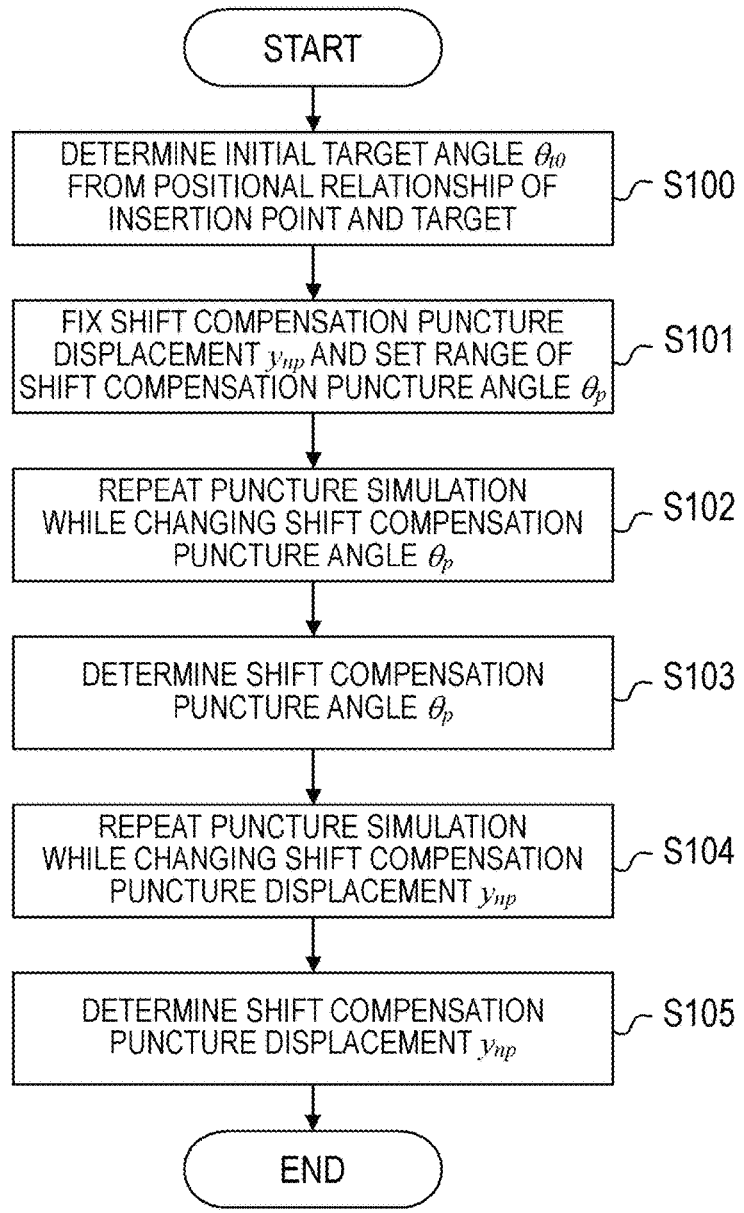
FIG. 10 is a flow chart depicting a flow of puncture control according to Embodiment 2.

The flow chart in FIG. 10 shows the procedure to determine the shift compensation puncture angle $\theta_p$ and the shift compensation puncture displacement $y_{np}$. First the puncture simulation unit 130 determines the initial target angle $\theta_{r0}$ based on the positional relationship of the insertion point and the target (step S100). Then the puncture simulation unit 130 fixes the shift compensation puncture displacement $y_{np}$ to an infinitesimal value, and sets the angle range of the shift compensation puncture angle $\theta_p$ to the range of Expression (10) (step S101).

$$\theta_{r0}-\theta_s<\theta_p<\theta_{r0}+\theta_s \qquad (10)$$

In Expression (10), $\theta_s$ is a search range. As the search range $\theta_s$ increases, the shift compensation displacement of the target can be increased, but the possibility of puncturing an organ by the side face of the puncture needle also increases. Hence in this embodiment, $\theta_s$ is set to ⅔ πrad. The puncture simulation unit 130 executes the simulation using the control system shown in FIG. 9A, and calculates the puncture error (step S102). At this time, the simulation is repeated with slightly changing the shift compensation puncture angle $\theta_p$ within the range of Expression (10), whereby the puncture error is acquired for each shift compensation puncture angle $\theta_p$. The puncture simulation unit 130 selects the angle $\theta_p$ at which the puncture error is the minimum as the optimum value of the shift compensation puncture angle (step S103).

Then the puncture simulation unit 130 determines the optimum value of the shift compensation puncture displacement $y_p$ using the determined shift compensation puncture angle $\theta_p$. In concrete terms, the puncture simulation unit 130 fixes the shift compensation puncture angle $\theta_p$, and repeats the simulation with increasing the shift compensation puncture displacement $y_{np}$ a little at a time from 0, and calculates the puncture error at each displacement $y_{np}$ (step S104). The shift compensation puncture displacement $y_{np}$ is changed in a range where the organ is not punctured. For example, the value of the puncture reaction force $F_n$ is calculated, and the simulation is ended when this values reaches a predetermined value (e.g. 10N). The puncture simulation unit 130 selects the displacement $y_{np}$ with which the puncture error is smallest as the optimum value of the shift compensation puncture displacement (step S105). By this processing described above, the shift compensation puncture angle $\theta_p$ and the shift compensation puncture displacement $y_{np}$, to minimize the puncture error, can be determined.

Figure 9B:
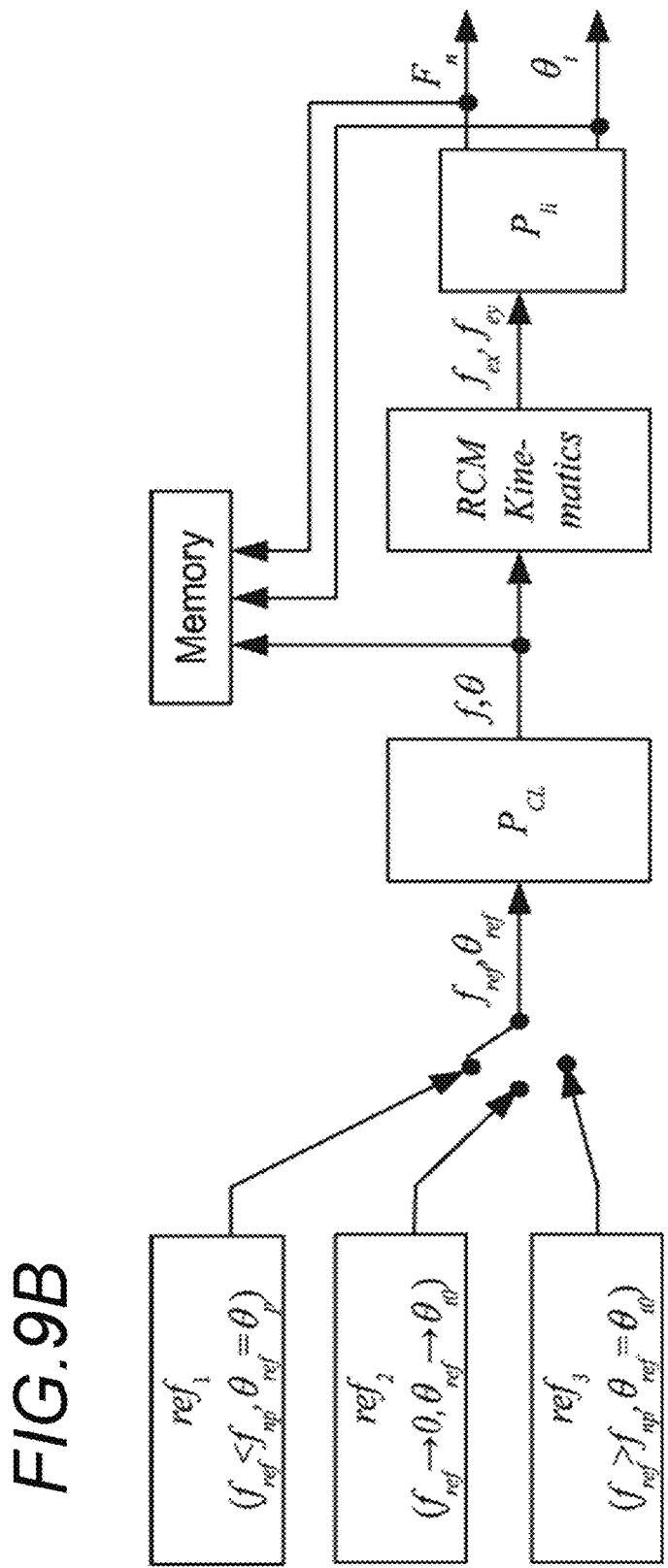

In FIG. 9A, the shift compensation puncture is performed by controlling the needle advancement displacement y and the needle angle $\theta_p$, but the needle puncture force f may be controlled instead of the needle advancement displacement y. The needle puncture force f is a force that acts in the insertion direction of the puncture needle 110. FIG. 9B shows the block diagram of the control system that controls the needle puncture force f and the needle angle θ. Here $f_{np}$ denotes the shift compensation puncture force (first target force) in the reference signal. By performing a processing similar to FIG. 10 using the control system in FIG. 9B, the optimum values of the shift compensation puncture force $f_{np}$ and the shift compensation angle $\theta_p$ can be determined.

3) Simulation

Figure 11A:
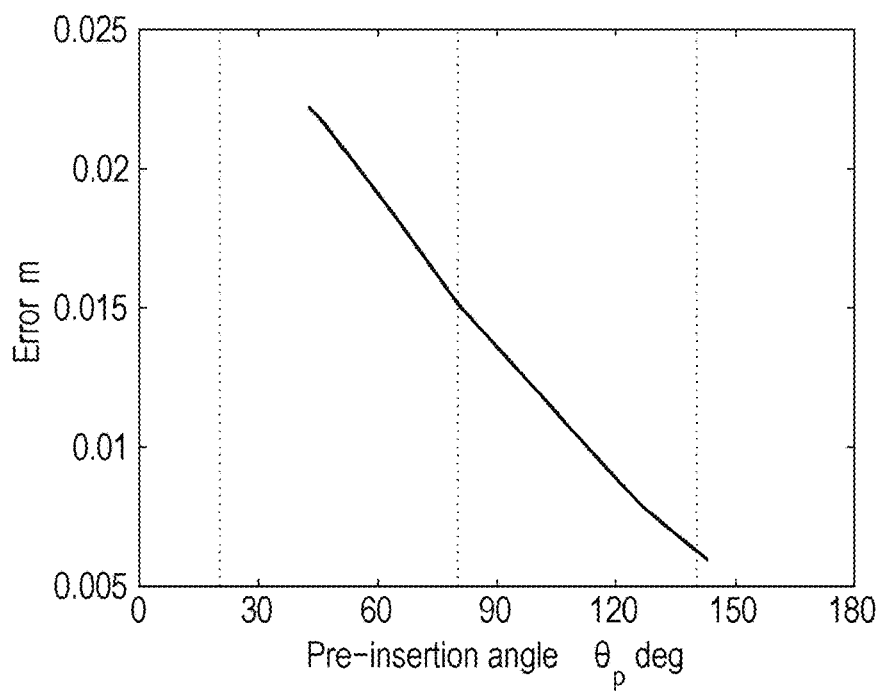
FIG. 11A and FIG. 11B each show the result of the simulation of Embodiment 2.

The result of simulation using the control system mentioned in the previous section is shown. First FIG. 11A shows the result that is acquired by fixing the shift compensation puncture displacement $y_{np}$ to an infinitesimal value, and repeating simulation with slightly changing the shift compensation puncture angle $\theta_p$. The abscissa indicates the shift compensation puncture angle $\theta_p$, and the ordinate indicates the puncture error. The puncture error does not indicate a puncture error at the point when the shift compensation puncture based on the reference signal $ref_1$ ends, but indicates the final error when simulation, until the target is punctured based on the reference signals $ref_2$ and $ref_3$, is executed. The initial target angle $\theta_{r0}$ of the target is set to 80.11 deg in this embodiment, and is indicated by the broken line in FIG. 11A, along with the search ranges $\theta_{r0}-\theta_s$ and $\theta_{r0}+\theta_s$ shown in Expression (10). The target of this embodiment shifts in the −x direction if punctured with maintaining the initial target angle without performing the shift compensation puncture. Therefore the shift compensation puncture must be shifted in the +x direction, for which a large shift compensation puncture angle $\theta_p$ should be taken. As the simulation result in FIG. 11A shows, the puncture error decreases as the shift compensation puncture angle $\theta_p$ is increased. In this embodiment, the optimum shift compensation puncture angle $\theta_p$ is 135.5 deg, because of the restriction in the mesh count of the finite element model, but the mesh may be sub-divided to compute the shift compensation puncture angle $\theta_p$.

Figure 11B:
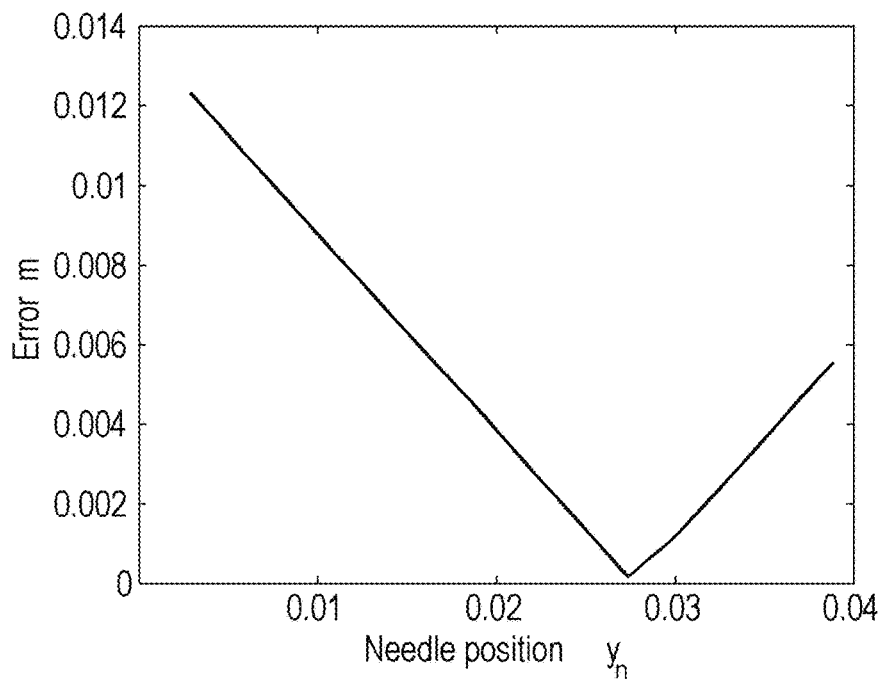

Then the optimum shift compensation puncture displacement $y_{np}$ is searched using the acquired shift compensation puncture angle $\theta_p$. FIG. 11B shows a result acquired by repeating the simulation with increasing the shift compensation puncture displacement $y_{np}$ from 0. The abscissa indicates the shift compensation puncture displacement $y_{np}$, and the ordinate indicates the puncture error. As FIG. 11B shows, the puncture error with respect to the target becomes the minimum when the shift compensation puncture displacement $y_{np}$ is 0.0273 m.

Figure 12:
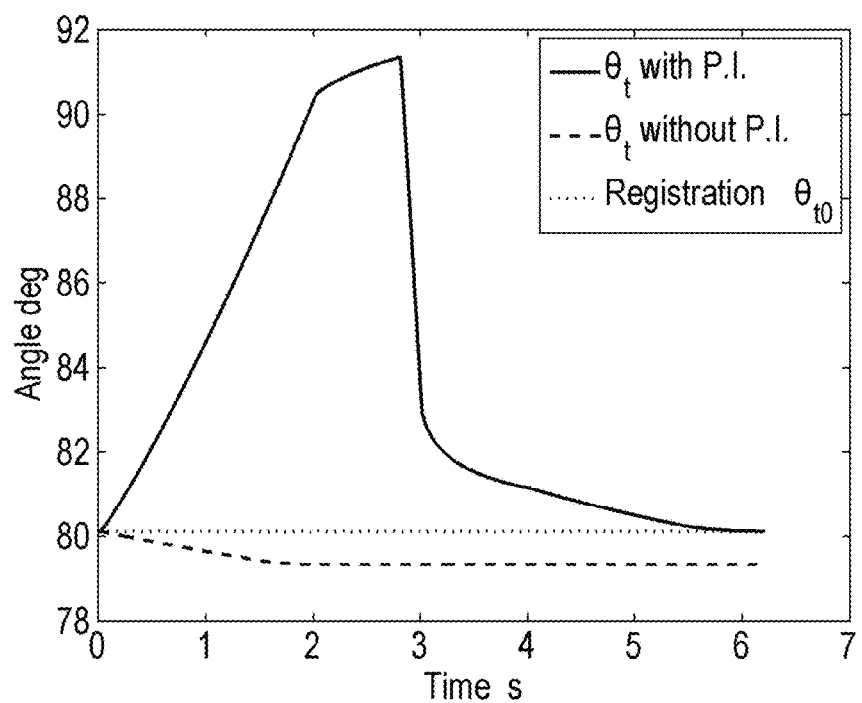
FIG. 12 shows the result of the simulation of Embodiment 2.

In FIG. 12, the target angle $\theta_t$ result by the control system of this embodiment with respect to time is indicated by the solid line. When the simulation is started, the puncture needle is controlled at the shift compensation puncture angle $\theta_p$, and reaches the shift compensation puncture displacement $y_{np}$ in two seconds. Then the puncture needle stops until 2.8 seconds. The control thus far is performed based on the reference signal $ref_1$. During the time between 2.8 seconds and 4 seconds, a reverse movement of the puncture needle and a rotation of the puncture needle from the shift compensation puncture angle $\theta_p$ to the initial target angle $\theta_{r0}$ are controlled based on the reference signal $ref_2$. After 4 seconds, puncture is performed based on the reference signal $ref_3$, and the control system advances the needle until the puncture reaction force $F_n$ reaches the puncture generating reaction force (e.g. 10N). In the period from 5.6 seconds to 6.1 seconds, which is a time zone when the possibility of puncture generation increases, the puncture error has sufficiently been reduced. As a comparison, response when the puncture was performed with maintaining the puncture angle at the initial target angle $\theta_{r0}$, is shown by the broken line. In this case, the target shifts as the needle advances, and puncture error remains in the time zone when the possibility of puncture generation increases.

Figure 13A:
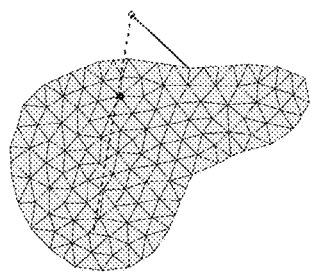
FIG. 13A to FIG. 13L each show the result of the simulation of Embodiment 2.
Figure 13B:
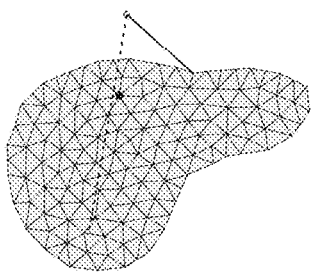
Figure 13C:
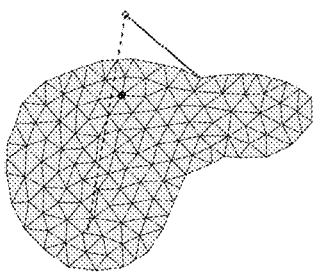
Figure 13D:
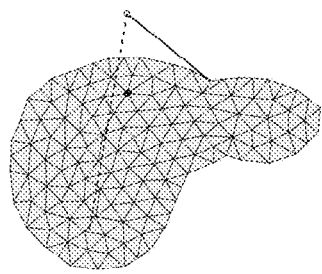
Figure 13E:
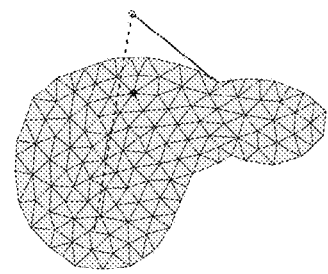
Figure 13F:
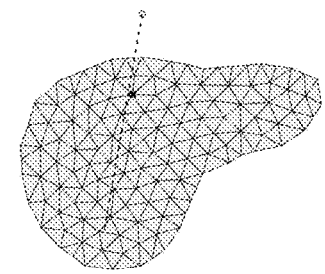
Figure 13G:
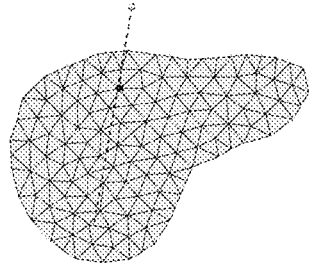
Figure 13H:
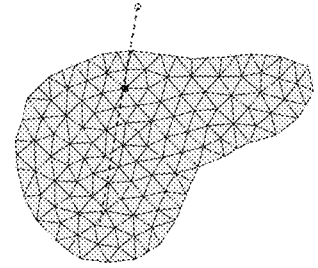
Figure 13I:
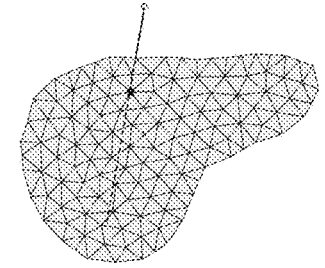
Figure 13J:
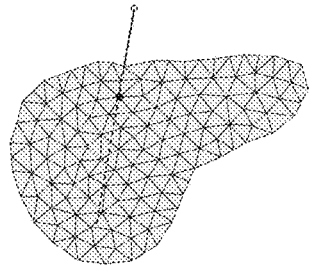
Figure 13K:
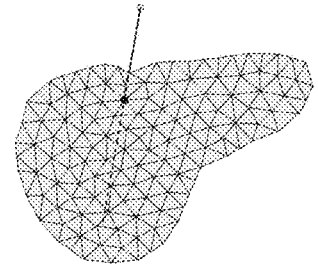
Figure 13L:
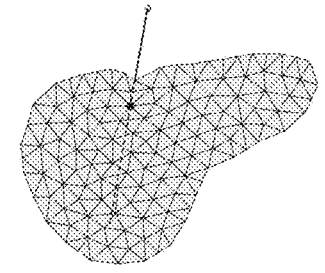

FIG. 13A to FIG. 13L show responses from the start of the simulation at every 0.5 seconds. The responses based on the reference signals $ref_1$, $ref_2$ and $ref_3$ correspond to FIG. 13A to FIG. 13E, FIG. 13F to FIG. 13H, and FIG. 13I to FIG. 13L respectively. The orientation of the puncture needle is indicated by the solid line, the path according to the initial target angle is indicated by the broken line, and the target is indicated by a dot. As FIG. 13A to FIG. 13E show, the target is shifted in the +x direction by the shift compensation puncture. From FIG. 13I, the puncture needle advances on the path according to the initial target angle $\theta_{r0}$. In the state when the puncture needle starts insertion shown in FIG. 13I, the target deviates from the path in the +x direction, but the target returns to the path as the puncture needle advances, as shown in FIG. 13J and FIG. 13K. Then in the time zone in FIG. 13L, when the possibility of puncture generation increases, the puncture error has been sufficiently reduced. This shows that the puncture needle control system of this embodiment is effective. Moreover, the puncture accuracy can be improved by using the result acquired by the simulation as an actual puncture planning signal.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-142425, filed on Jul. 10, 2014, and Japanese Patent Application No. 2015-083663, filed on Apr. 15, 2015, which are hereby incorporated by reference herein in their entirety.

What is claimed is:

1. A puncture system comprising:
a simulation unit that performs simulation of movement of an organ and a puncture needle when the puncture needle is inserted into the organ and advanced toward a target segment inside the organ, by simulation using an organ model;
a planning unit that plans a movement of the puncture needle when an actual organ is punctured, and outputs a planning result; and
a control unit that controls the movement of the puncture needle on a basis of the planning result,
wherein the simulation unit executes a plurality of times of the simulation in which conditions of an advancement speed of the puncture needle are mutually different and generates a plurality of simulation results, and
wherein the planning unit plans the movement of the puncture needle on a basis of a selected one of the plurality of simulation results, at least one puncture error and puncture time period of which meets a predetermined criteria,
wherein the simulation unit performs speed adjustment in performing the simulation, so as to reduce the advancement speed of the puncture needle in accordance with a puncture reaction force, which is a force that the puncture needle receives from the organ,
wherein the simulation unit adjusts the advancement speed of the puncture needle by multiplying a predetermined initial value of the advancement speed by a speed gain which is determined in accordance with the puncture reaction force,
wherein the speed gain is determined by the following expressions, and
the simulation unit executes the plurality of times of simulation while changing, as the condition, a value of a parameter $a_k$ in the following expressions:

$$K_f = 1 \quad (F_n \leq F_{nimin})$$

$$K_f = a_k F_n - a_k F_{nmin} + 1 \quad \left(F_{nmin} < F_n < \frac{a_k F_{nmin} - 1 + K_{fmin}}{a_k}\right)$$

$$K_f = K_{fmin} \quad \left(F_n \geq \frac{a_k F_{nmin} - 1 + K_{fmin}}{a_k}\right)$$

where $K_f$ is a speed gain, $F_n$ is a puncture reaction force, $F_{nmin}$ is a predetermined threshold, $a_k$ is a parameter to determine the reduction rate of the speed gain, and $K_{fmin}$ is a predetermined minimum value of the speed gain.

2. The puncture system according to claim 1, wherein the simulation unit executes the plurality of times of simulation while changing, as the condition, a parameter which determines a reduction rate of the advancement speed in the speed adjustment.

3. The puncture planning apparatus according to claim 1, wherein the planning unit selects a simulation result in which an error of the angle of the puncture needle with respect to the target segment is minimal at a point when the puncture needle punctures the organ.

4. The puncture planning apparatus according to claim 1, wherein the planning unit selects a simulation result in which time required for puncture is shortest out of the simulation results in which an error of the angle of the puncture needle with respect to the target segment is within a predetermined range at a point when the puncture needle punctures the organ.

5. The puncture planning apparatus according to claim 1, wherein the planning unit selects a simulation result in which both an error of the angle of the puncture needle with respect to the target segment at a point when the puncture needle punctures the organ, and a maximum value of an error of the angle of the puncture needle with respect to the target segment after the puncture needle contacts the organ, are within a predetermined range.

6. The puncture planning apparatus according to claim 1, wherein the planning unit outputs information that represents the angle of the puncture needle and an advancement displacement or the advancement speed of the puncture needle in each time step, as the planning result.

* * * * *